(12) United States Patent
Tan et al.

(10) Patent No.: US 12,734,357 B2
(45) Date of Patent: Sep. 15, 2026

(54) MRI COMPATIBLE MAGNET FOR COCHLEAR IMPLANT

(71) Applicant: ZHEJIANG NUROTRON BIOTECHNOLOGY CO., LTD., Hangzhou (CN)

(72) Inventors: Zhiping Tan, Hangzhou (CN); Daomin Zhou, Hangzhou (CN); Xiaoan Sun, Hangzhou (CN); Shuqi Qi, Hangzhou (CN); Chu Li, Hangzhou (CN)

(73) Assignee: ZHEJIANG NUROTRON BIOTECHNOLOGY CO., LTD., Hangzhou (CN)

( * ) Notice: Subject to any disclaimer, the term of this patent is extended or adjusted under 35 U.S.C. 154(b) by 290 days.

(21) Appl. No.: 18/571,239

(22) PCT Filed: Aug. 17, 2021

(86) PCT No.: PCT/CN2021/112907

§ 371 (c)(1),
(2) Date: Dec. 17, 2023

(87) PCT Pub. No.: WO2022/262106

PCT Pub. Date: Dec. 22, 2022

(65) Prior Publication Data

US 2024/0278006 A1 Aug. 22, 2024

(30) Foreign Application Priority Data

Jun. 16, 2021 (CN) ........................ 202110663473.X

(51) Int. Cl.
*A61N 1/08* (2006.01)
*H01F 7/02* (2006.01)

(52) U.S. Cl.
CPC .............. *A61N 1/08* (2013.01); *H01F 7/021* (2013.01)

(58) Field of Classification Search
None
See application file for complete search history.

(56) References Cited

U.S. PATENT DOCUMENTS

| | | | | |
|---|---|---|---|---|
| 11,792,586 B2 * | 10/2023 | Kennes | .............. | A61N 1/36038 381/324 |
| 2016/0144170 A1 * | 5/2016 | Gibson | ................ | A61N 1/3787 607/57 |
| 2019/0076649 A1 | 3/2019 | Lee et al. | | |

FOREIGN PATENT DOCUMENTS

| | | |
|---|---|---|
| CN | 112354079 | 2/2021 |
| CN | 212542072 | 2/2021 |
| CN | 213374741 | 6/2021 |

* cited by examiner

*Primary Examiner* — Erica S Lee
(74) *Attorney, Agent, or Firm* — Jiwen Chen; Joywin IP Law PLLC

(57) ABSTRACT

The present invention discloses an MRI compatible magnet for a cochlear implant, comprising a base, an upper shell, a bracket, a magnet, needle rollers and a lower shell, wherein the upper shell and the lower shell form a closed space, and the magnet and the bracket are arranged in the closed space; the magnet is in an axisymmetric polygonal disk shape; the magnetic pole of the magnet is divided into two halves from the top view, one half is an N pole, and the other half is an S pole; the magnet is arranged in the bracket; the bracket is matched with the magnet in shape, and the bracket rotates with the magnet when the magnet rotates axially; a plurality of positioning slots are provided on the outer side face of the bracket; and , the needle rollers are accommodated in the positioning slots, and the needle rollers are cylindrical and can axially roll in the positioning slots without slipping off. The MRI compatible magnet for a cochlear implant provided by the present invention can flexibly rotate on the bracket according to the change of the direction of an external magnetic field, so that the N pole and the S pole of (Continued)

the magnet can be freely switched in the spatial direction, and it is unnecessary to take out the cochlear implant and the internal magnet during examinations in a strong magnetic field such as MRI.

10 Claims, 5 Drawing Sheets

MRI COMPATIBLE MAGNET FOR COCHLEAR IMPLANT

This is a U.S. national stage application of PCT Application No. PCT/CN2021/112907 under 35 U.S.C. 371, filed Aug. 17, 2021 in Chinese, claiming priority of Chinese Application No. 202110663473.X, filed Jun. 16, 2021, all of which are hereby incorporated by reference.

TECHNICAL FIELD OF THE INVENTION

The present invention belongs to the field of medical devices, and particularly relates to an MRI compatible magnet for a cochlear implant.

BACKGROUND OF THE INVENTION

A typical cochlear implant system includes an extracorporeal machine and an implant. The extracorporeal machine includes a transmitting coil and an MRI compatible magnet of an external cochlear implant. The magnetic resonance imaging (MRI) compatible magnet of the external cochlear implant is in a conventional coin shape, and has a north-south magnetic dipole which is perpendicular to the patient's skin to produce external magnetic field lines. The corresponding receiver component implant is implanted under the patient's skin. The receiver component implant includes a receiving coil and an MRI compatible magnet of an internal cochlear implant. The MRI compatible magnet of the internal cochlear implant also is in a coin shape, and has a north-south magnetic dipole which is perpendicular to the patient's skin to produce internal magnetic field lines. The MRI compatible magnets of the internal and external cochlear implants attract each other, so that the extracorporeal machine and the implant are fixedly connected.

However, a problem arises when the patient undergoes the magnetic resonance imaging (MRI) examination. That is, the MRI compatible magnet of the cochlear implant interacts with the external magnetic field applied to MRI, and the directional magnetization of the MRI compatible magnet of the cochlear implant is substantially perpendicular to the patient's skin. As a result, the external magnetic field from MRI can produce a torque on the MRI compatible magnet of the internal cochlear implant, and the torque can displace the MRI compatible magnet of the internal cochlear implant or the whole implant shell from the correct position, which might damage neighboring tissues in the body of the patient and even threaten life. In addition, the external magnetic field from MRI can reduce or eliminate the magnetization of the MRI compatible magnet of the cochlear implant, so that the extracorporeal machine can be no longer fixed at the correct position. Moreover, the MRI compatible magnet of the cochlear implant might cause imaging artifacts in MRI images, and might cause auditory hallucinations due to the interaction between the external magnetic field of MRI and the implant.

SUMMARY OF THE INVENTION

In order to solve the above problems, the present invention employs the following technical solutions. An MRI compatible magnet for a cochlear implant is provided, including a base, an upper shell, a bracket, a magnet, needle rollers and a lower shell, wherein, the upper shell and the lower shell form a closed space, and the magnet and the bracket are arranged in the closed space; the magnet is in an axisymmetric polygonal disk shape; the magnetic pole of the magnet is divided into two halves from the top view, one half is an N pole, and the other half is an S pole; the magnet is arranged in the bracket; the bracket is matched with the magnet in shape, and the bracket rotates with the magnet when the magnet rotates axially; a plurality of positioning slots are provided on the outer side face of the bracket; and, the needle rollers are accommodated in the positioning slots, and the needle rollers are cylindrical and can axially roll in the positioning slots without slipping off.

Preferably, the bracket and the magnet are directly injection-molded outside the magnet.

Preferably, a plurality of semicircular balls are arranged on the edges of the upper and lower surfaces of the bracket.

Preferably, the positioning slots are U-shaped internal buckles, and the needle rollers are buckled into the positioning slots.

Preferably, the magnet is in an octagonal disk shape.

Preferably, internal threads and internal conical surfaces are provided on the inner wall of the base.

Preferably, external threads and external conical surfaces which are matched with the internal threads and the internal conical surfaces of the base in shape are provided on the outer wall of the upper shell; and, when the upper shell is screwed into the base, the internal conical surfaces come into contact with the external conical surfaces to realize clamping fixation.

Preferably, bayonets are provided on the bracket, and the edges of the polygonal disk-shaped magnet are exposed at the bayonets.

Preferably, U-shaped slots are formed on the outer wall of the base.

Preferably, a flange is arranged in the middle of the exterior of the base, and positioning holes are formed on the flange.

The present invention has the following beneficial effects. The magnet in the existing cochlear implant is an ordinary magnet, and the implant needs to be taken out by surgery during MRI examination and implanted after MRI examination, thus resulting in multiple damages, aggravating the pain of the patient and improving the failure rate of the whole cochlear implant system. The MRI compatible magnet for a cochlear implant provided by the present invention is designed to adopt a polygonal magnet with N and S poles and can flexibly rotate on the bracket according to the change of the direction of the external magnetic field, so that the N pole and the S pole of the MRI compatible magnet for the cochlear implant can be freely switched in the spatial direction. Thus, the reliability of the cochlear implant device is improved, and it is unnecessary to take out the cochlear implant during various examinations with a magnetic field such as MRI, thereby avoiding multiple injuries and damages.

In addition, the magnets for cochlear implants in the prior art are easily demagnetized. According to the document "Demagnetization of cochlear implants and temperature changes in 3.0T MRI environment", the degree of demagnetization is positively related to the include angle A between the NS direction and the external static magnetic field B0. Since the N pole and the S pole can freely rotate under the action of the external magnetic field, the included angle A is minimized, so that the degree of demagnetization of the internal magnet is minimized.

DETAILED DESCRIPTION OF THE INVENTION

The preferred embodiments of the present invention will be described below in detail with reference to the accompanying drawings.

Figure 1:
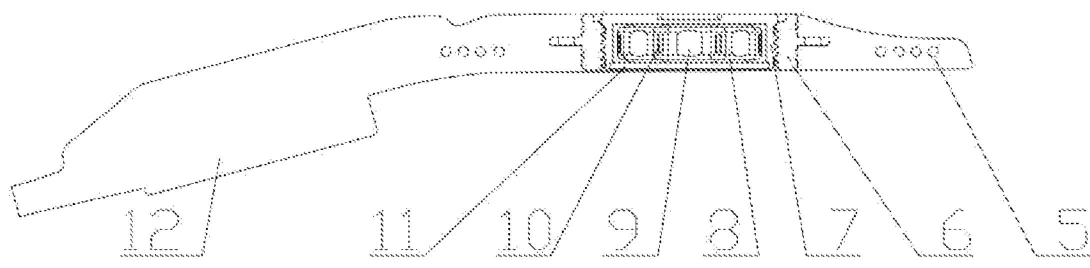
FIG. 1 is a schematic diagram of the overall structure of an MRI compatible magnet for a cochlear implant according to a specific embodiment of the present invention.

With reference to FIG. 1, the MRI compatible magnet for a cochlear implant includes a base 6, an upper shell 7, a bracket 8, a magnet 9, needle rollers 10 and a lower shell 11, wherein, the upper shell 7 and the lower shell 11 form a closed space, and the magnet 9 and the bracket 8 are arranged in the closed space; the magnet 9 is in an axisymmetric polygonal disk shape; the magnetic pole of the magnet 9 is divided into two halves from the top view, one half is an N pole, and the other half is an S pole; the magnet 9 is arranged in the bracket 8; the bracket 8 is matched with the magnet 9 in shape, and the bracket 8 rotates with the magnet 9 when the magnet 9 rotates axially; a plurality of positioning slots 8-3 are provided on the outer side face of the bracket 8; and, the needle rollers 10 are accommodated in the positioning slots 8-3, and the needle rollers 10 are cylindrical and can axially roll in the positioning slots 8-3 without slipping off. The implant further includes a stimulator 12 and a receiving coil 5.

Figure 2:
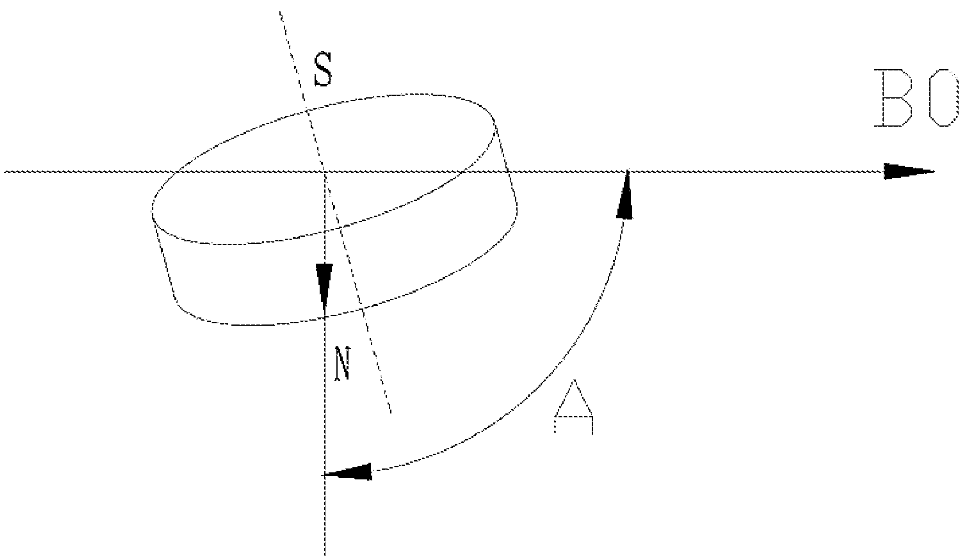
FIG. 2 is a schematic diagram of the magnet of the cochlear implant in the prior art and the static magnetic field.
Figure 3:
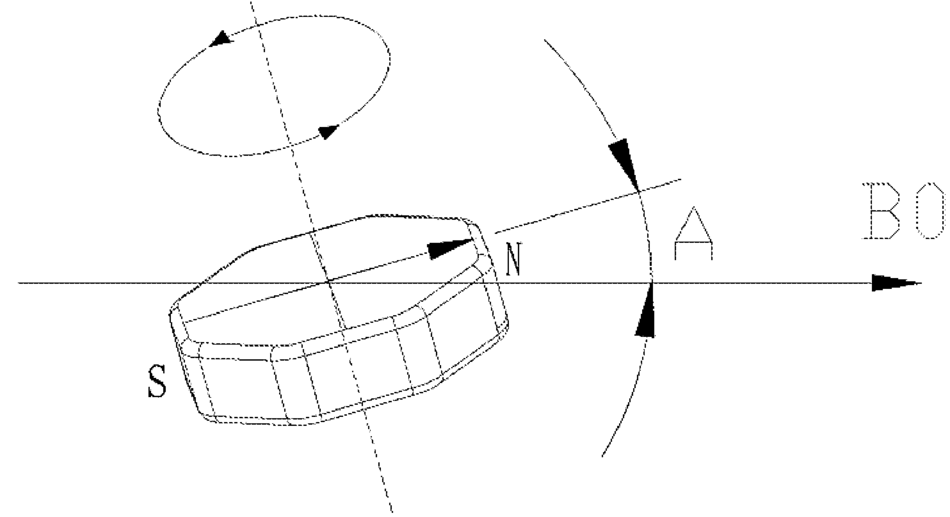
FIG. 3 is a schematic diagram of the magnet in the MRI compatible magnet for a cochlear implant and the static magnetic field according to a specific embodiment of the present invention.

With reference to FIG. 2 and FIG. 3, FIG. 2 is a relationship diagram of the internal magnet of the cochlear implant in the prior art and the magnetic field. The magnetization direction of the magnetic poles of the internal magnet is the up-down direction. In the example of FIG. 2, the upper half is an S pole, and the lower half is an N pole. If the direction of the magnetic lines of the external static magnetic field is denoted by B0, the included angle A between the NS direction of the internal magnet and the external magnetic field B0 is always 90 degrees, so that the effect of not taking out the internal magnet during MRI examination cannot be achieved. Otherwise, a serious damage will be caused to the human body. In FIG. 3, the magnetization direction of the magnetic poles of the magnet in the present invention is a horizontal direction. Even if the included angle A between the initial NS direction and the external static magnetic field is 90 degrees, since the magnet 13 can rotate, that is, the N pole and the S pole can freely rotate, the included angle A between the final NS direction and B0 is 0 degree, and the magnetic torque is T=F*R*sin(A). The magnetic torque changes from the initial T=F*R to 0, so it is hardly stressed during MRI examination or in a similar strong magnetic field environment.

Figure 4:
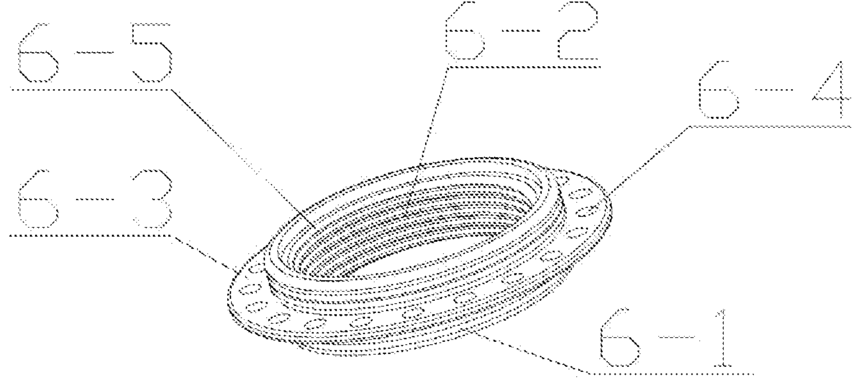
FIG. 4 is a schematic structure diagram of the base of the MRI compatible magnet for a cochlear implant according to a specific embodiment of the present invention.
Figure 5:
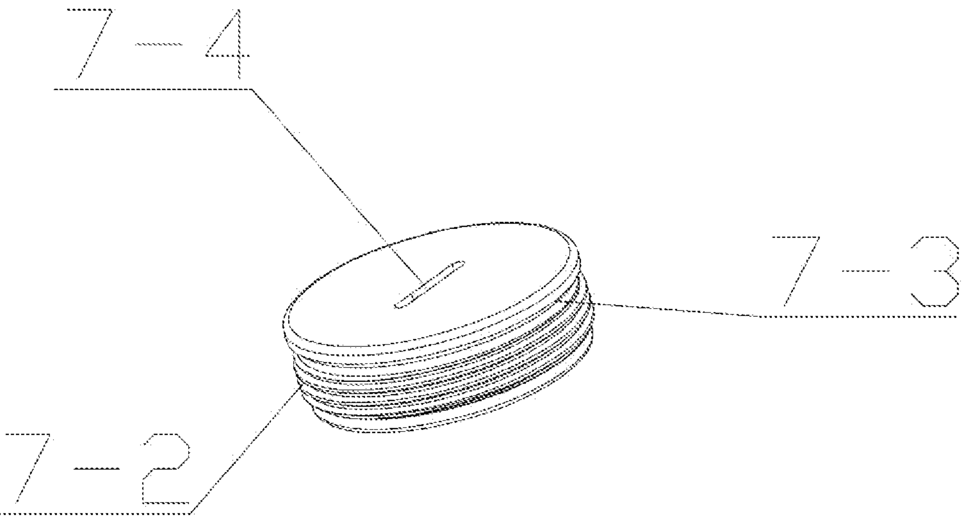
FIG. 5 is a schematic structure diagram of the upper shell of the MRI compatible magnet for a cochlear implant according to a specific embodiment of the present invention.
Figure 6:
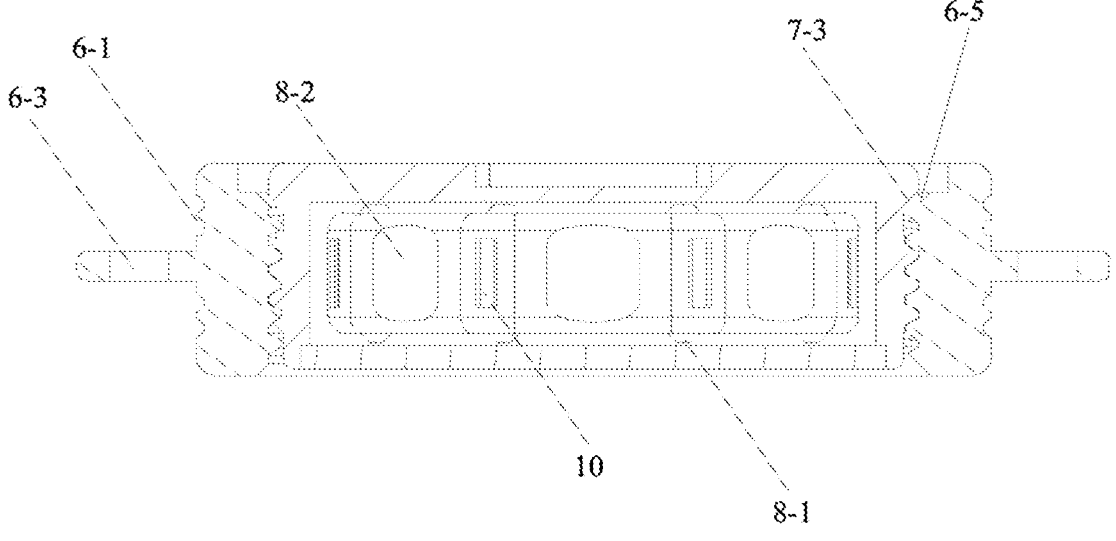
FIG. 6 is a schematic assembly diagram of the base and the upper shell of the MRI compatible magnet for a cochlear implant according to a specific embodiment of the present invention.

With reference to FIGS. 4-6, internal threads 6-2 and internal conical surfaces 6-5 are provided on the inner wall of the base 6. External threads 7-2 and external conical surfaces 7-3 which are matched with the internal threads 6-2 and the internal conical surfaces 6-5 of the base 6 in shape are provided on the outer wall of the upper shell 7. When the upper shell 7 is screwed into the base 6, the internal conical surfaces 6-5 come into contact with the external conical surfaces 7-3 to realize clamping fixation. A I-shaped slot 7-4 through which the upper shell 7, the magnet 9 and the lower shell 11 are screwed in or out as a whole by a screw driver is formed on the upper surface of the upper shell 7. After the magnet 9 is injection-molded with the bracket 8 and after the needle rollers 10 are assembled in the positioning slots 8-3 of the bracket 8, the whole is put in the upper shell 7. The upper shell 7 and the lower shell 11 are made of a titanium alloy material, and are fixedly connected by laser welding.

Since the upper shell 7 is made of titanium alloy and the base 6 is made of PEEK (polyetheretherketone), during MRI detection, the overlap of the projection areas of the upper shell 7 and the base 6 will produce artifacts in the images of the detection results, so that the MRI detection results are greatly affected. In the present invention, the area of the top surface of the upper shell 7 is the same as the area of the top surfaces of the internal conical surfaces 6-5 of the base 6, and the projections of the top surface of the upper shell 7 and the top surfaces of the internal conical surfaces 6-5 are not overlapped, thereby avoiding artifacts during MRI detection.

Figure 7:
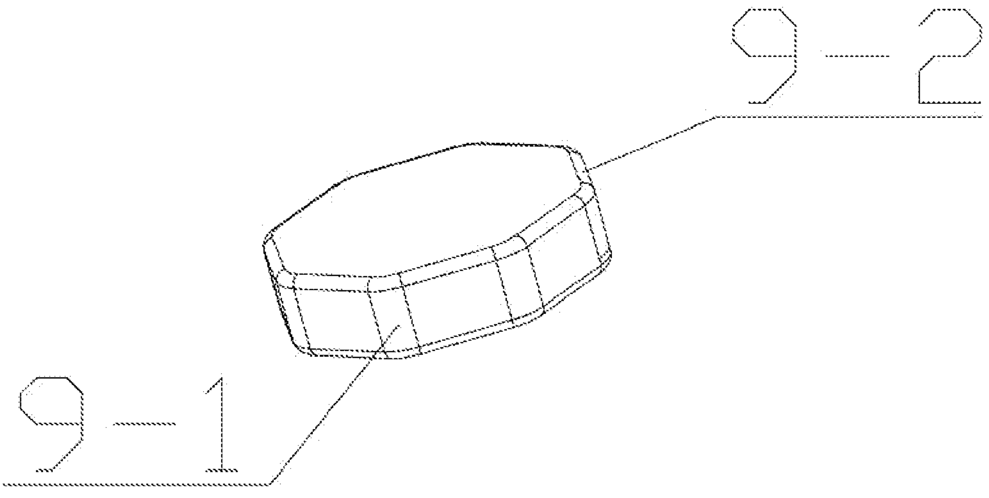
FIG. 7 is a schematic structure diagram of the magnet of the MRI compatible magnet for a cochlear implant according to a specific embodiment of the present invention.
Figure 8:
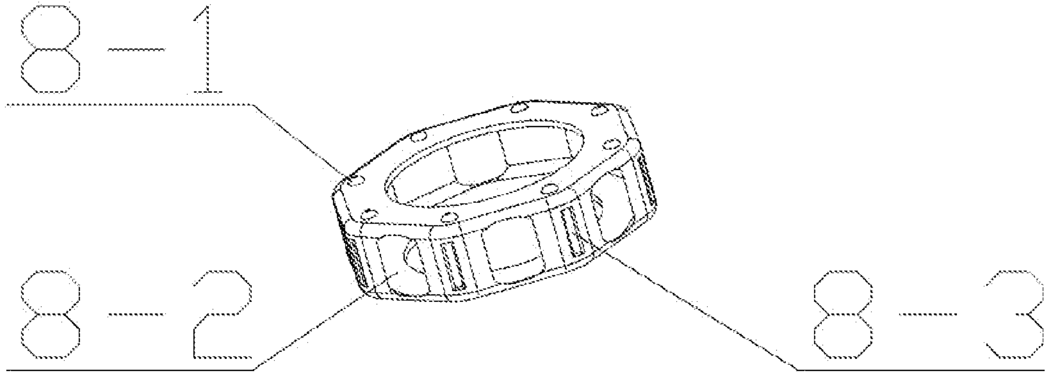
FIG. 8 is a schematic structure diagram of the bracket of the MRI compatible magnet for a cochlear implant according to a specific embodiment of the present invention.
Figure 9:
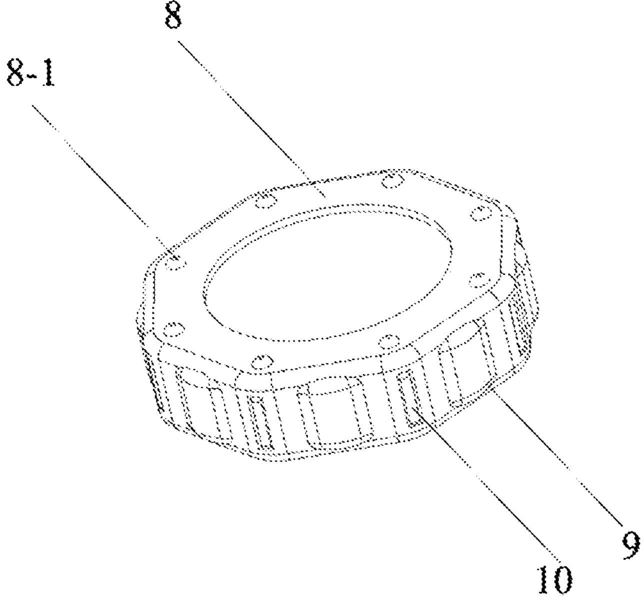
FIG. 9 is a schematic structure diagram of the magnet and the bracket of the MRI compatible magnet for a cochlear implant after injection molding according to a specific embodiment of the present invention.

With reference to FIGS. 7-9, the bracket 8 and the magnet 9 are directly injection-molded outside the magnet 9. Bayonets 8-2 are provided on the bracket 8, and the edges of the polygonal disk-shaped magnet 9 are exposed at the bayonets 8-2. The corners of the polygonal disk-shaped magnet 9 are all wrapped and fixed by the bracket 8 during injection molding, so that the inclusion degree of the bracket 8 and the magnet 9 is ensured, and the rotation effect and flexibility will not be affected by the bracket 8 made of PEEK when the magnet 9 drives the bracket 8 to rotate. Fillet structures 9-1 and 9-2 are provided at the edges and corners of the magnet 9.

A plurality of semicircular balls 8-1 are arranged on the edges of the upper and lower surfaces of the bracket 8, so that the friction of the bracket 8 when rotating on the upper shell 7 and the lower shell 11 is reduced.

Figure 10:
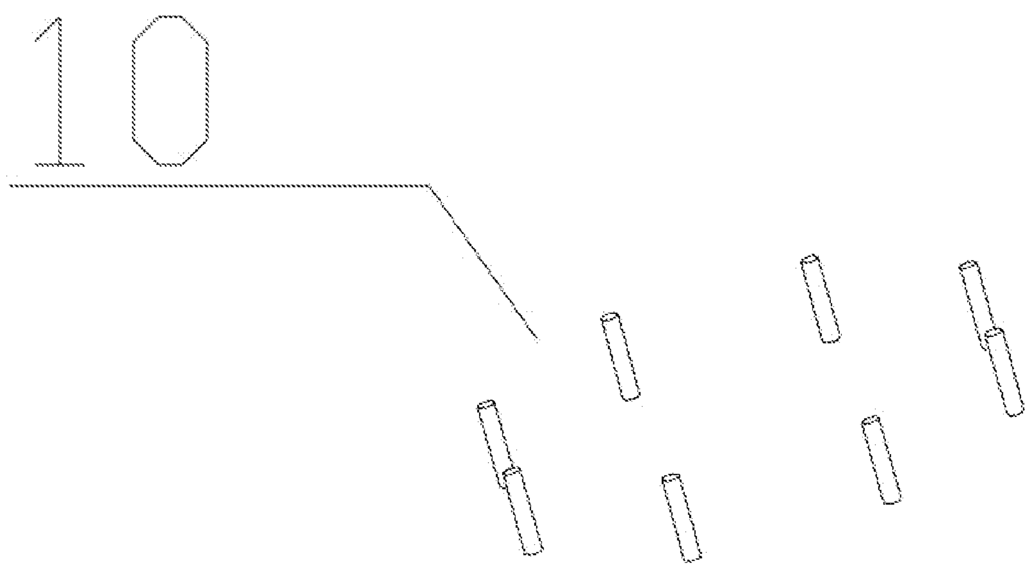
FIG. 10 is a schematic structure diagram of the needle rollers of the MRI compatible magnet for a cochlear implant according to a specific embodiment of the present invention.
Figure 11:
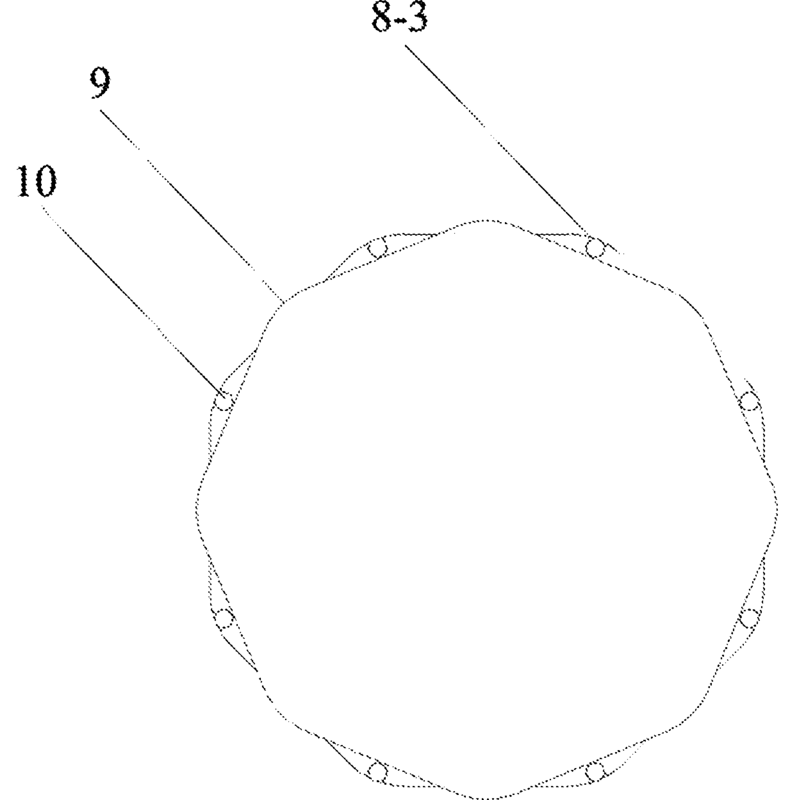
FIG. 11 is a schematic assembly diagram of the needle rollers and the bracket of the MRI compatible magnet for a cochlear implant according to a specific embodiment of the present invention.

With reference to FIGS. 10 and 11, the positioning slots 8-3 on the bracket 8 are U-shaped internal buckles, and the needle rollers 10 are buckled into the positioning slots 8-3. This arrangement is convenient for assembling, and the contact between the bracket 8 and the inner sidewall of the upper shell 7 is planar. When the needle rollers 10 roll, a uniform sliding surface is formed on the inner sidewall of the upper shell 7. Compared with the technical solution of providing balls in the prior art, the arrangement of the needle rollers 10 in the present invention stabilizes the bracket 8 during its rotation, and will not cause irregular friction to wear and damage the inner sidewall of the upper shell 7.

In a specific embodiment, the magnet 9 is in an octagonal disk shape, eight bayonets 8-2 are arranged on the bracket 8, and eight needle rollers 10 are provided.

U-shaped slots 6-1 are formed on the outer wall of the base 6, a flange 6-3 is arranged in the middle of the exterior of the base 6, and positioning holes 6-4 are formed on the flange 6-3. With the above arrangement, the base 6 can be firmly injection-molded into the silicone of the implant, and is impossible to fall off when in normal use.

During examinations with magnetic fields such as MRI or in a magnetic environment, the polygonal magnet 9 can rotate freely according to the magnetism to adapt to the magnetic field, without affecting the structure and electrical reliability of the cochlear implant and affecting the examination results in the magnetic field. Thus, any magnetic field and any angle can be adapted.

It is to be noted that the above preferred embodiments are merely used for describing, rather than limiting, the technical solutions of the present invention. Although the present invention has been described in detail by the above preferred embodiments, it should be understood by those skilled in the art that various alternations can be made in form and detail without departing from the scope defined by the claims of the present invention.

The invention claimed is:

1. An MRI compatible magnet for a cochlear implant, comprising a base, an upper shell, a bracket, a magnet, needle rollers and a lower shell, wherein, the upper shell and the lower shell form a closed space, and the magnet and the bracket are arranged in the closed space; the magnet is in an axisymmetric polygonal disk shape; the magnetic pole of the magnet is divided into two halves from a major plane of the magnet, one half is an N pole, and the other half is an S pole; the magnet is arranged in the bracket; the bracket is matched with the magnet in shape, and the bracket rotates with the magnet when the magnet rotates axially; a plurality of positioning slots are provided on an outer side face of the bracket; and, the plurality of positioning slots, with a corresponding plurality of needle rollers, each of the plurality of needle rollers are accommodated in a respective plurality of positioning slots, and the needle rollers are cylindrical and can axially roll along longitudinal axes in the positioning slots without slipping off from the positioning slots.

2. The MRI compatible magnet for a cochlear implant according to claim 1, wherein the magnet is wrapped and fixed by the bracket during injection molding.

3. The MRI compatible magnet for a cochlear implant according to claim 1, wherein the bracket comprises upper and lower surfaces and a plurality of semicircular balls are arranged on edges of the upper and lower surfaces of the bracket.

4. The MRI compatible magnet for a cochlear implant according to claim 1, wherein the positioning slots are U-shaped internal buckles, and the needle rollers are buckled into the respective positioning slots.

5. The MRI compatible magnet for a cochlear implant according to claim 1, wherein the magnet is in an octagonal disk shape.

6. The MRI compatible magnet for a cochlear implant according to claim 1, wherein internal threads and internal conical surfaces are provided on an inner wall of the base.

7. The MRI compatible magnet for a cochlear implant according to claim 6, wherein external threads and external conical surfaces which are matched with the internal threads and the internal conical surfaces of the base in shape are provided on an outer wall of the upper shell; and, when the upper shell is screwed into the base, the internal conical surfaces come into contact with the external conical surfaces to realize clamping fixation.

8. The MRI compatible magnet for a cochlear implant according to claim 1, wherein bayonets are provided on the bracket, and edges of the polygonal disk-shaped magnet are exposed at the bayonets.

9. The MRI compatible magnet for a cochlear implant according to claim 1, wherein U-shaped slots are formed on an outer wall of the base.

10. The MRI compatible magnet for a cochlear implant according to claim 1, wherein a flange is arranged in a middle position of an exterior of the base, and positioning holes are formed on the flange.

* * * * *